(12) United States Patent
Rome et al.

(10) Patent No.: US 7,503,596 B2
(45) Date of Patent: Mar. 17, 2009

(54) LOCKING LUER FITTING

(75) Inventors: Guy T. Rome, West Valley City, UT (US); Sandra J. Rome, Taylorsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/046,269

(22) Filed: Mar. 11, 2008

(65) Prior Publication Data

US 2008/0150281 A1 Jun. 26, 2008

Related U.S. Application Data

(63) Continuation of application No. 11/036,164, filed on Jan. 14, 2005, now Pat. No. 7,347,458.

(51) Int. Cl.
*F16L 19/00* (2006.01)

(52) U.S. Cl. ............... 285/384; 285/353; 285/85; 604/533; 604/241

(58) Field of Classification Search ........... 285/384, 285/353, 85, 86, 92; 604/533, 241, 242
See application file for complete search history.

(56) References Cited

U.S. PATENT DOCUMENTS

| 980,677 | A | * | 1/1911 | Rhoads ............... 285/86 |
| 1,580,694 | A | * | 4/1926 | Smith ............... 251/89.5 |
| 1,664,125 | A | * | 3/1928 | Lowrey ............... 285/13 |
| 1,666,802 | A | * | 4/1928 | Von Allmen ........... 285/384 |
| 2,118,350 | A | * | 5/1938 | Holt ............... 285/39 |
| 4,553,587 | A | * | 11/1985 | Traylor ............... 165/95 |
| 5,188,398 | A | * | 2/1993 | Parimore et al. ............ 285/39 |
| 5,620,427 | A | * | 4/1997 | Werschmidt et al. ........ 604/535 |
| 5,957,716 | A | * | 9/1999 | Buckley et al. ............ 439/321 |
| 6,293,595 | B1 | * | 9/2001 | Marc et al. ............... 285/92 |
| 7,347,458 | B2 | * | 3/2008 | Rome et al. ............... 285/384 |

\* cited by examiner

*Primary Examiner*—David E Bochna
(74) *Attorney, Agent, or Firm*—Rutan & Tucker LLP

(57) ABSTRACT

A fluid line connector to establish fluid communication with a conventional male luer fitting. The fluid line connector includes a housing with a hub member having a proximal opening adapted to receive a distal portion of the male luer fitting, a threaded profile circumscribing the proximal opening, and a cam member. The cam member engages the threaded surface of the male luer fitting collar to prevent inadvertent disengagement of the male luer fitting from the housing.

15 Claims, 13 Drawing Sheets

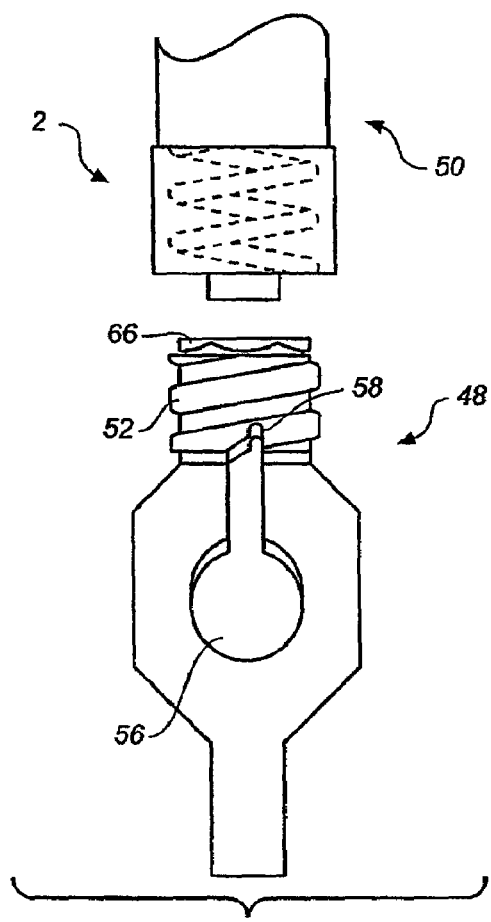 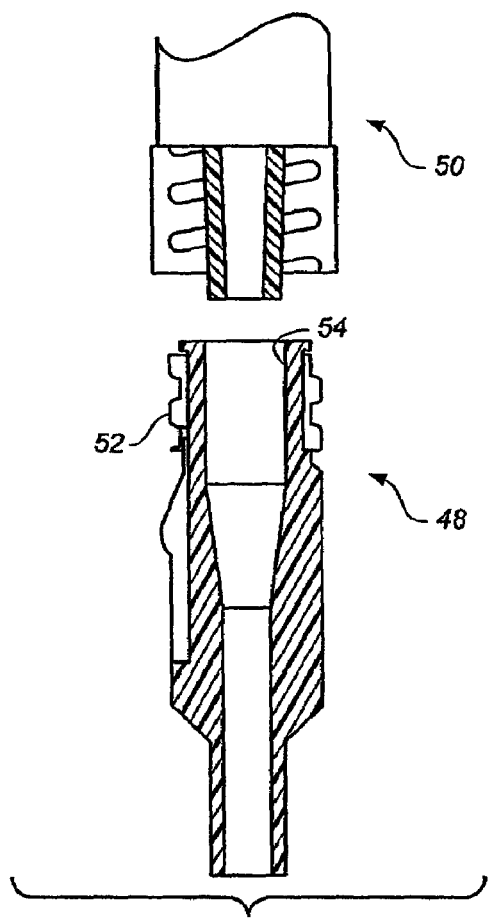
FIG. 3A    FIG. 3B
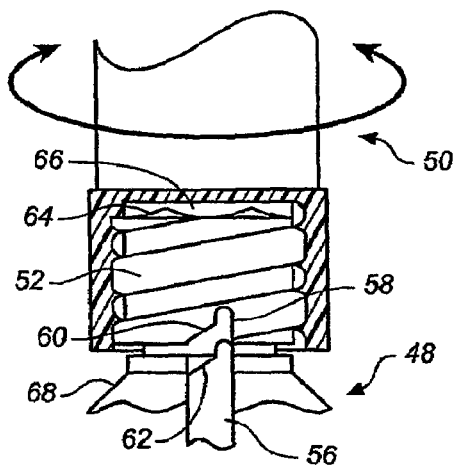 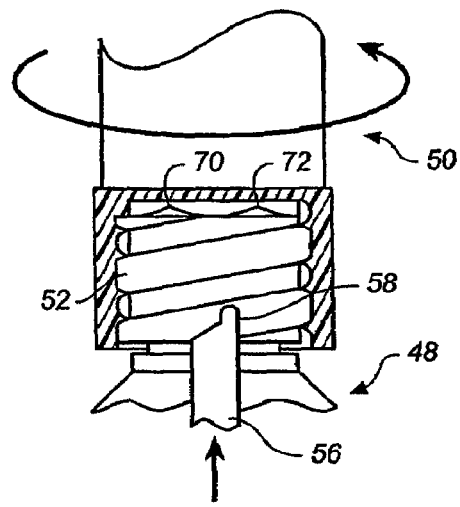
FIG. 4A    FIG. 4B

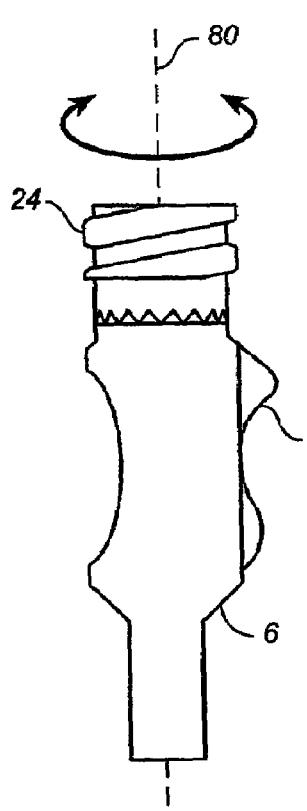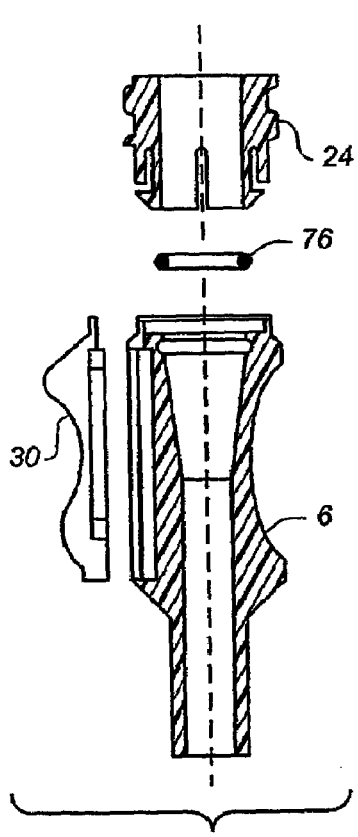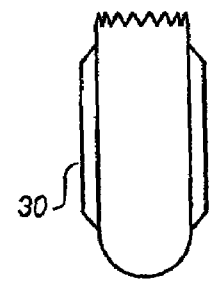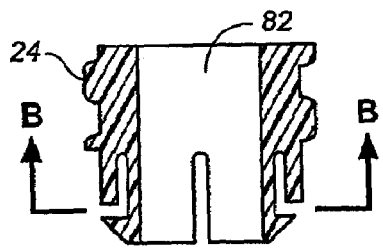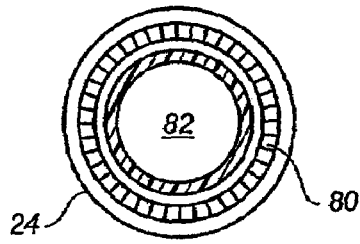

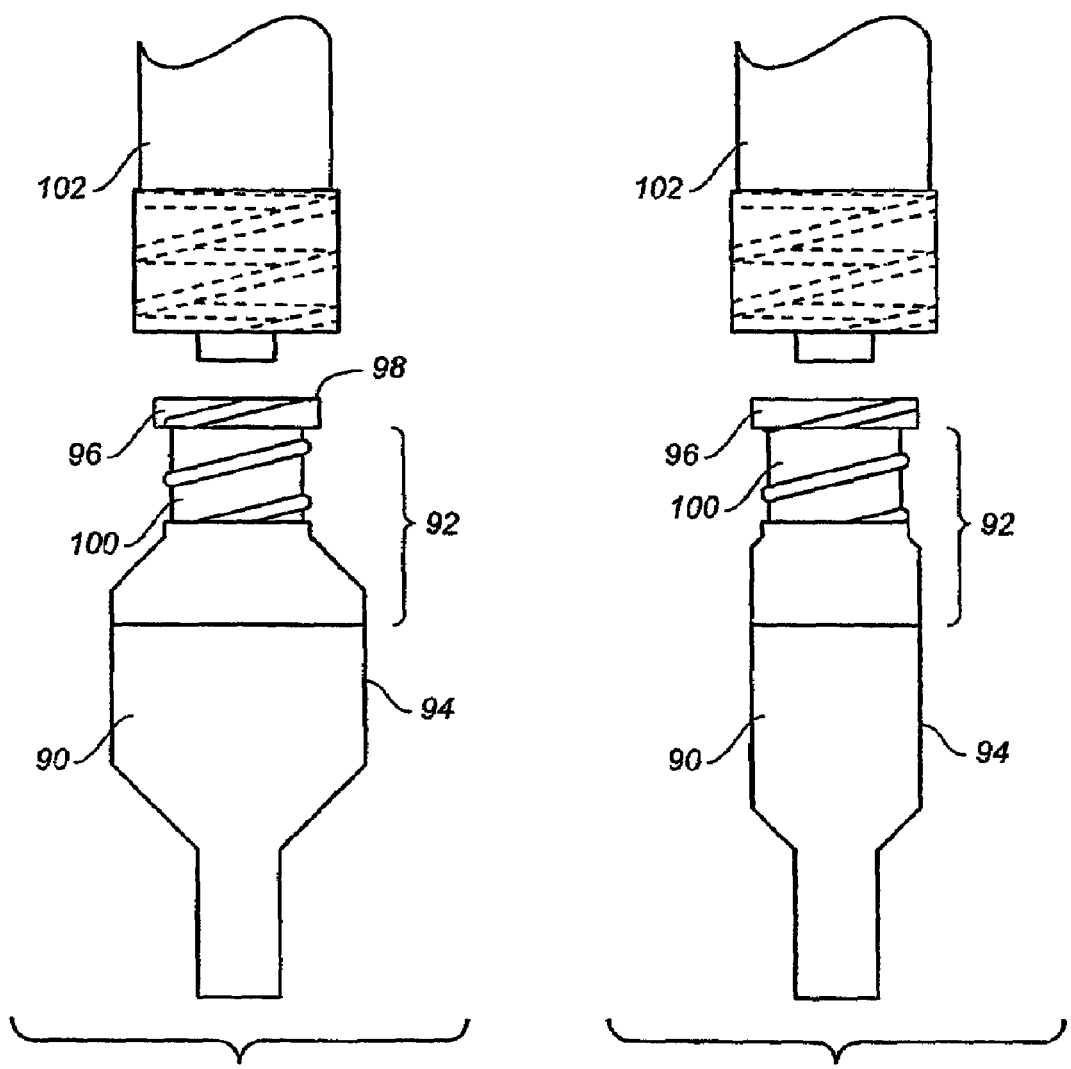
FIG. 12A  FIG. 12B
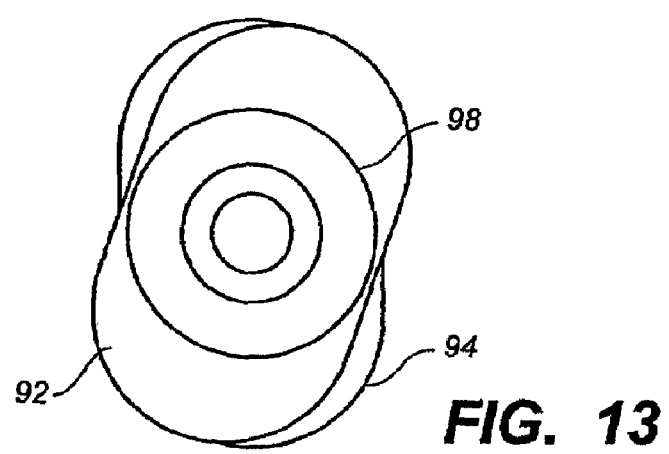
FIG. 13

FIG. 14A  FIG. 14B

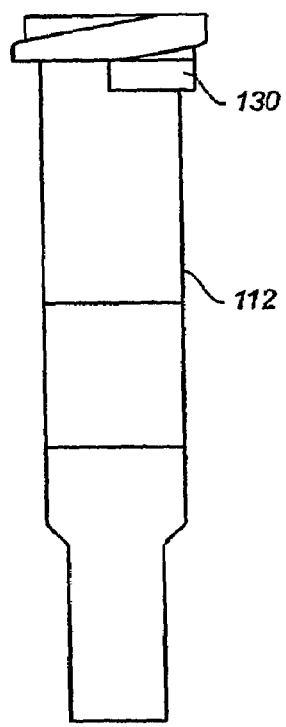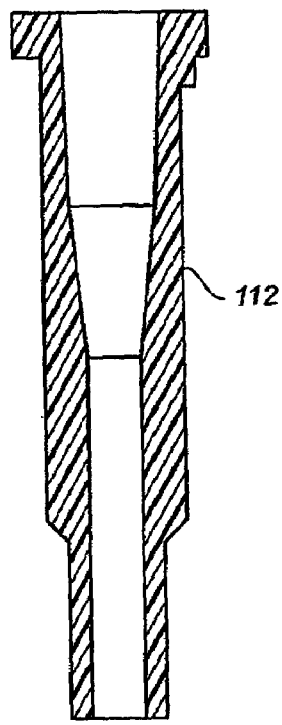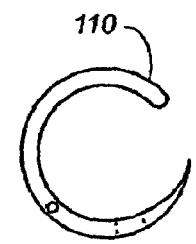
FIG. 16A  FIG. 16B  FIG. 17A
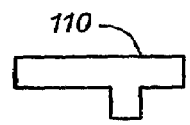
FIG. 17B
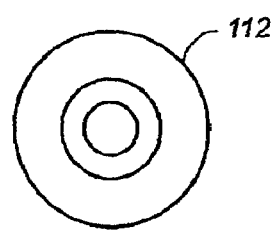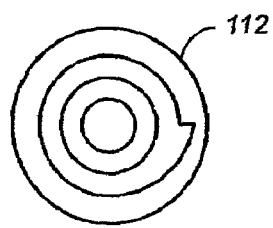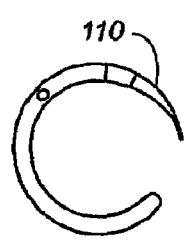
FIG. 16C  FIG. 16D  FIG. 17C

LOCKING LUER FITTING

CROSS-REFERENCE TO RELATED APPLICATIONS

This application is a continuation of U.S. patent application Ser. No. 11/036,164, filed Jan. 14, 2005, now U.S. Pat. No. 7,347,458, which is incorporated by reference into this application as if fully set forth herein.

BACKGROUND OF THE INVENTION

Typical luer lock connectors, which are commonly utilized in medical and industrial settings, do not have a locking mechanism to prevent accidental disconnections. The typical luer lock connection interface comprises (1) a male luer connector having a rounded and tapered mating surface and a threaded locking collar, and (2) a corresponding female luer connector having a lumen to receive the rounded and tapered mating surface on the male luer connector and ears or threads on an outer surface for engaging the threaded locking collar on the male connector in order to achieve a positive connection. However, once the male luer connector is threaded onto the female luer connector, there are no built-in mechanisms to prevent the connection from loosening and disconnecting from each other.

There are a variety of conditions where secured fluid connection interfaces capable of preventing accidental disconnection are desirable. For example, in the hospital setting, medication infusion lines may be accidentally disconnected due to patient movements, inadequate tightening of the luer connector fitting, etc. These unintentional disconnections of catheter lines may affect the outcome of patient treatment, and in certain situations could result in death. In industrial settings, vibrations, stress on the fluid lines, inadequate tightening of the luer connector fitting, etc., may also result in loosening and eventual separation of the connection interface. A compromise of the fluid lines can result in leakage of chemicals into the environment. In situations where the fluid lines are carrying toxic materials, the consequence could be detrimental.

Therefore, a luer fitting connection with a built-in mechanism to prevent accidental disconnection of the luer connection is desirable. In addition, interfaces designed to assist the user in achieving proper tightening of luer fittings are also desirable.

SUMMARY OF THE INVENTION

Luer connection interfaces utilizing various mechanisms to prevent inadvertent disconnections are disclosed herein. In one variation, a rotating thread section allows a secure connection to be maintained after attachment. This design may incorporate a rotating thread section on the female luer fitting that permits the male luer fitting to be threaded thereon, but revolves with the male luer fitting when the male luer fitting rotates to disconnect. This rotation in the opposite direction causes the rotating thread portion to 'lock' against the threads of the male luer fitting and prevent disconnection. To remove the male luer fitting, a locking mechanism (e.g., locking slide or pin, latch, etc.) is introduced to engage the rotating thread section and prevent the rotation thereof, so that the user can unthread the male luer fitting and disengage the male luer fitting from the female luer fitting. In one variation, a one-way latch is utilized as a locking mechanism to engage the rotating thread section.

In another variation, a rotating thread luer lock design incorporates a partially rotatable lower thread segment that can be rotated in the opposite direction of the thread rotation and effectively lock the threads on the male luer connector in a fixed position in relation to the female luer connector. To release the male luer connection, the lower thread segment on the female luer connector is aligned with the top portion of the thread segment, thereby allowing the male luer connector to be unscrewed.

In yet another variation, the locking mechanism comprises a locking cam is slidably disposed on the female luer connector. The slidable cam engages the threads on the male luer connector when it is rotated onto the female luer connector. The displacement of the slidable cam locks the male luer connector in place and prevents loosening of the connection interface. To disconnect the male luer connector, the slidable cam is displaced to release the cam action, allowing the male connector to be rotated and detached from the female connector.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 3A shows a frontal view of another variation of a locking luer fitting comprising a male luer connector (top) and a corresponding female luer connector with a rotatable collar (bottom). In this variation, a spring loaded locking slide is implemented to restrain the clockwise rotation of the rotatable collar so that a male luer connector can be threaded thereon. The receiving notch on the rotatable collar is profiled to allow rotation of the rotatable collar unless the locking slide is being held in place by the user.

FIG. 3B shows a cross-sectional view of the locking luer fitting of FIG. 3A.

FIG. 4A illustrates the capability for the male luer connector to freely rotate while connected to the female luer connector on the female luer. The male luer connector is able to maintain the connection without unthreading from the rotatable collar.

FIG. 4B illustrates a positive pressure being applied on the sliding lock to engage the rotatable collar and prevent the rotatable collar from rotating in either direction, such that the male luer can be unthreaded from the rotatable collar.

FIG. 6A is the side view of the female luer connector of FIG. 5A illustrating the freely revolving rotatable collar.

FIG. 6B is a cross-sectional view of the female luer connector of FIG. 6A, shown with the parts disassembled. In this variation, an elastomeric ring is implemented to maintain a seal between the male and the female connector.

FIG. 7 shows the female luer connector of FIG. 5A with the locking slide detached from its corresponding hosing.

FIG. 8A. is a cross-sectional view illustrating the rotatable collar from FIG. 5A.

FIG. 8B is a cross-sectional view of the rotatable collar of FIG. 8A taken at "B-B". The rotatable collar is viewed along its longitudinal axis toward its proximal end.

FIG. 12A illustrates another variation of the locking luer fitting with a partially rotatable thread segment that can be rotated in the opposite direction of the thread rotation, thereby effectively locking the engaging thread on the male connector in position.

FIG. 12B shows the side view of the locking luer fitting of FIG. 12A.

FIG. 13 is a top view of the female luer connector of FIG. 12A, shown with the rotating locking collar rotated to displace the thread segment on the rotating locking collar from the upper thread segment on the housing of the female connector.

FIG. 16A shows a side view of the internal hub from FIG. 15.

FIG. 16B shows a cross-sectional view of the internal hub of FIG. 16A.

FIG. 16C shows a top view of the internal hub of FIG. 16A.

FIG. 16D shows a bottom view of the internal hub of FIG. 16A.

FIG. 17A shows a top view of the locking ring from FIG. 15.

FIG. 17B shows a side view of the locking ring of FIG. 17A.

FIG. 17C shows a bottom view of the locking ring of FIG. 17A.

DETAILED DESCRIPTION OF THE INVENTION

Figures 1A, 1B, 1C:
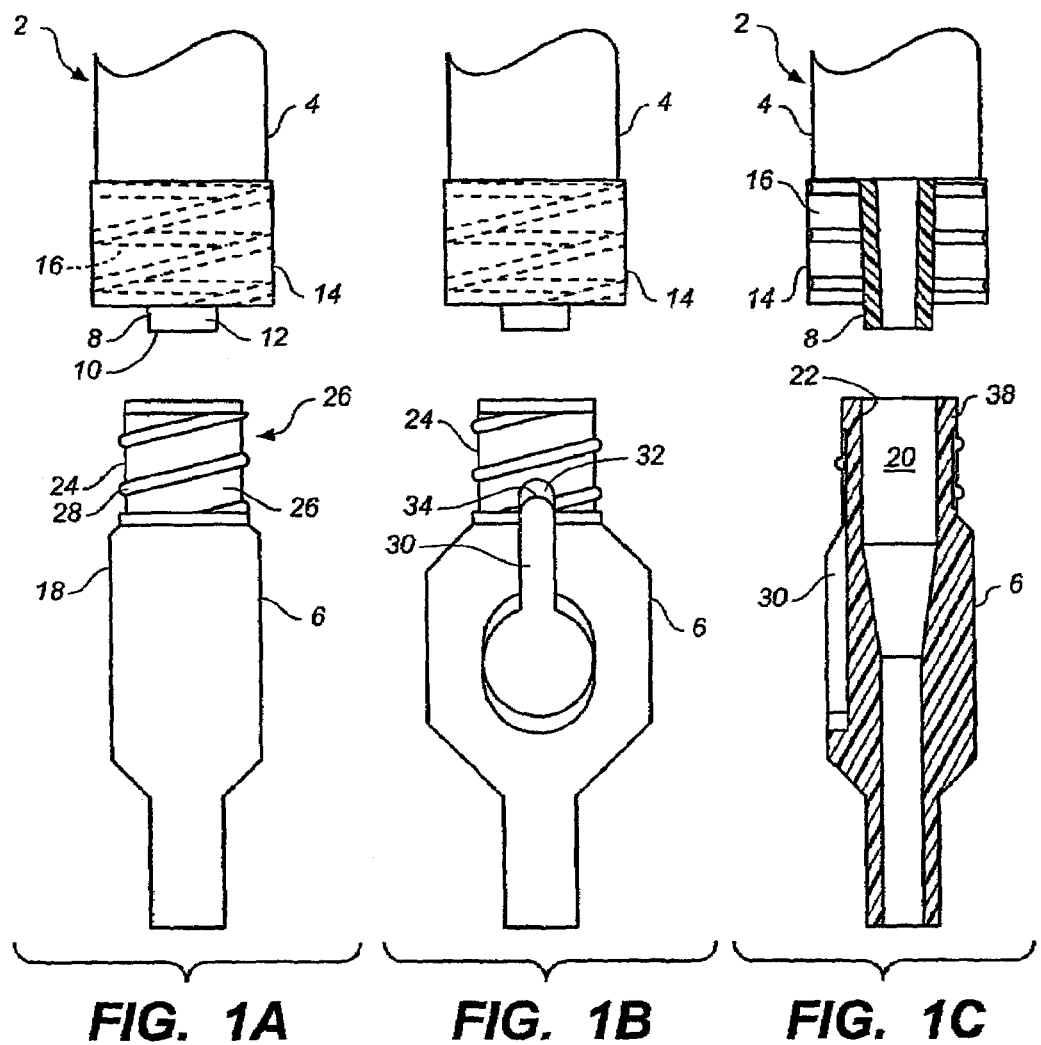
FIG. 1A shows a side view of one variation of a locking luer fitting comprising a male luer connector (top) and a corresponding female luer connector with a rotatable collar (bottom).
FIG. 1B shows a frontal view the locking luer fitting of FIG. 1A. A locking slide is positioned on the female luer connector for engaging the rotatable cuff.
FIG. 1C shows a cross-sectional view of the locking luer fitting of FIG. 1A.

The following detailed description should be read with reference to the drawings, in which identical reference numerals refer to like elements through out the different figures. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various tubing, catheters, drug pumps, infusion devices, etc.

Medical applications, such as connecting a male luer connector to a female luer connector on a catheter hub, are used herein as example applications. One of ordinary skill in the art having the benefit of this disclosure would appreciate that the various locking luer fitting described herein may be applicable in industrial settings and other situations where fluid line connection is needed.

It must also be noted that, as used in this specification and the appended claims, the singular forms "a," "an" and "the" include plural referents unless the context clearly dictates otherwise. Thus, for example, the term "a lumen" is intended to mean a single lumen or a combination of lumens, "a fluid" is intended to mean one or more fluids, or a mixture thereof.

The locking luer fitting may be implemented on a catheter assembly to facilitate the establishment of a fluid channel for the introduction/removal of a fluid into/from a patient's body. The female or male portion of the locking luer fitting may be temporarily attached to the proximal end of the catheter or it may be integrated within the proximal portion of the catheter body. In one aspect of the invention, a female luer connector with a locking luer interface may be attached to the proximal end of a catheter, such that the catheter can be easily accessed by connecting a male luer connector to establish a secured fluid connection. Bi-directional flow may be achieved with the implementation of multi-lumen male/female luer connectors. For example, corresponding male and female locking luer fitting connectors having two, three, or four lumens may be utilized to establish a secured fluid connection interface for multi-lumen catheter connections.

In one aspect of the invention, a fluid line connector is integrated with a safety feature to prevent unintentional disconnection. In one variation, the fluid line connector 2 comprises a male portion 4 and a female portion 6, as shown in FIG. 1A. The male portion 4 comprises a hollow elongated cylinder 8. The distal 10 portion of the hollow elongated cylinder includes a tapered mating surface 12. A locking collar 14, which includes a threaded inner surface 16, is positioned around the distal portion of the hollow elongated cylinder 8 to engage the female portion 6 of the connector. The locking collar 14 may be fixedly or rotatable disposed around the hollow elongated cylinder 8. The female portion 6 comprises a housing 18 including a lumen 20 configured to receive the distal section of the hollow elongated cylinder 8 from the male connector 4. The lumen 20 includes an inner surface 22 which matches the tapered mating surface 12 on the hollow elongated cylinder 8. A rotatable collar 24 is disposed at a proximal portion 26 of the housing 18. The rotatable collar 24 includes an outer surface profile 26 matching the threaded inner surface 16 on the male connector's locking collar 14. In one variation, the outer surface profile 26 on the rotatable collar 24 comprises a projecting helical rib 28. In another variation, the outer surface profile 26 on the rotatable collar 24 comprises a plurality of ears extending radially for engaging the locking collar 14 on the male portion 4 of the connector 2.

In the particular variation introduced above, a locking mechanism 30 is provided on the female portion 6 of the fluid line connector 2 for engaging the rotatable collar 24 and allowing the user to selectively prevent the rotation of the collar 24, as shown in FIG. 1B. In FIG. 1C, a cross-sectional view of the fluid line connector 2 is illustrated. The locking mechanism 30 may comprise one or more of the various mechanical interlocks for engaging the rotatable collar 24 and keeping the rotatable collar 24 in place. For example, the locking mechanism may comprise a locking slide 30, as shown in FIG. 1B, or a pin slidably disposed on the housing 18. Other mechanical interfaces well known to one of ordinary skill in the art that can be coupled to the housing and configured for engaging the rotatable collar are also contemplated herein. In this variation of the present invention, a surface indentation 32 is provided on the rotatable collar 24 for receiving the locking mechanism 30. The surface indentation 32 may comprise a notch or gap and may include a profile matching the surface profile at the proximal end 34 of the locking mechanism 30.

Figure 2A:
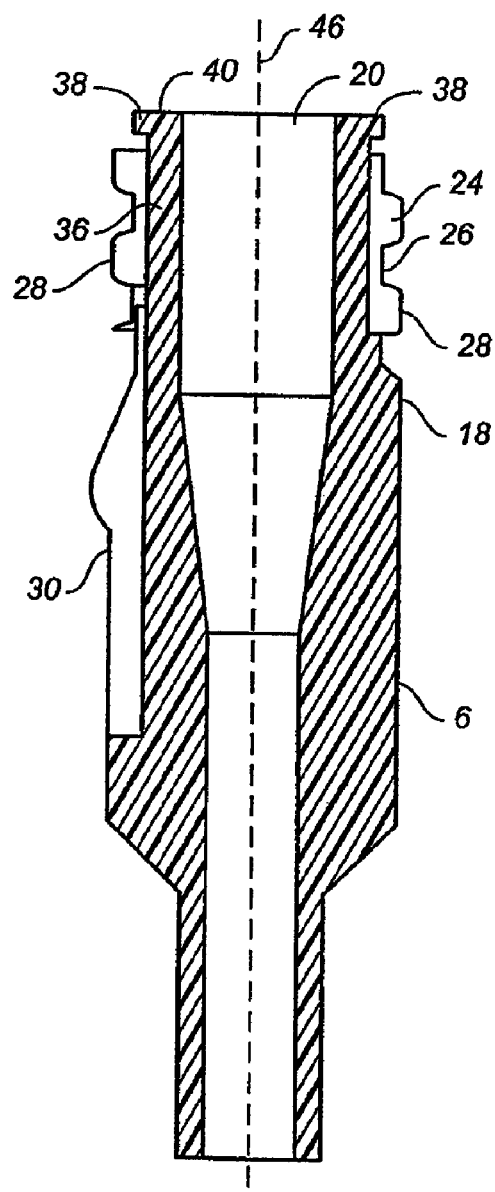
FIG. 2A illustrates one variation of a female luer connector with rotatable collar positioned at the neck portion of the housing.
Figure 2B:
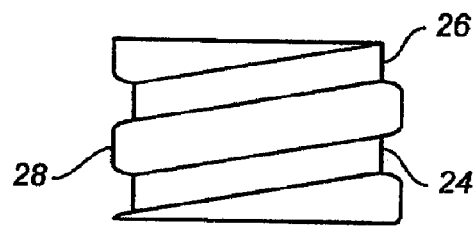
FIG. 2B shows a side view of the rotatable collar from FIG. 2A. The rotatable collar is shown detached from the main housing.
Figure 2C:
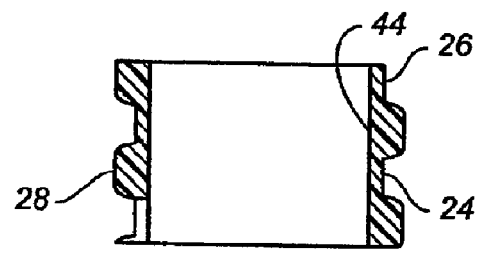
FIG. 2C shows a cross-sectional view of the rotatable collar of FIG. 2B.
Figure 2D:
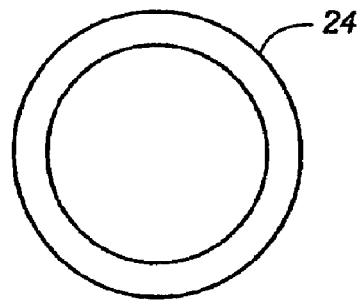
FIG. 2D shows the bottom view of the rotatable collar of FIG. 2B. The rotatable collar is viewed along its longitudinal axis into the lumen opening.

The housing 18 is configured with a neck portion 36 for supporting the rotatable collar 24. A ledge 38 extends radially at the proximal end 40 of the housing 18 to maintain the rotatable collar 24 on the housing 18. FIG. 2B is a side view of the rotatable collar 24 implemented in FIG. 2A. As shown, threads 28 are implemented on the outer surface 26 of the rotatable collar 24. The threads 28 may be configured to match the typical threads that are implemented on a standard male luer lock connector. FIG. 2C shows the cross-sectional view of the rotatable collar 24, and FIG. 2D is the bottom view of the rotatable collar 24. Other mechanisms may also be utilized to maintain the rotatable collar on the housing. For example, the outer surface of the neck portion 36 and the inner surface 44 of the rotatable collar 24 may include matching surface profiles to prevent the rotatable collar 24 from dislodging from the housing 18.

In the variation shown in FIG. 1A, the collar 24 is allowed to freely rotate 180 degrees or more around a longitudinal axis 46 of the female connector 6. To engage the male portion 4 of the connector, the locking slide 30 is displaced in the proximal direction and into the notch 32 on the rotatable collar 24 to prevent the rotatable collar 24 from revolving so that the locking collar 14 on the male portion 4 of the connector can be threaded onto the rotatable collar 24 on the housing 18. Once the male portion 4 is secured onto the rotatable collar 24, the locking mechanism 30 is retracted and the male portion 4, along with the rotatable collar 24, can rotate freely about the longitudinal axis 46 of the fluid line connector. An optional elastomeric ring or valve may be positioned within the lumen of the housing to provide additional sealing action between the hollow elongated cylinder and the lumen wall.

When the user is ready to disconnect the male portion 4 from the female portion 6, the user can displace the locking slide 30 to engage the notch 32 on the rotatable collar 24 again. Once the rotatable collar 24 is held in place, the male portion 4 can be unthreaded from the female portion 6. The locking slide 30 may be actively displaced (e.g., biased, etc.) in the distal direction such that a force in the proximal direction is needed to displace the locking slide 30 in the proximal direction into the notch 32 on the rotatable collar 24. This may prevent the locking slide 30 from accidentally engaging the rotatable collar 24. For example, the locking slide may be spring loaded. In another design, an elastic connection is utilized to couple the locking slide to the housing. In addition, one or more surface indentations may be provided on the rotatable collar 24 for receiving the locking mechanism 30. For example, a plurality of notches may be distributed around the circumference at the distal end of the rotatable collar. Having more than one notch capable of receiving the locking slide may allow the user to easily engage the rotatable collar without much effort in aligning the notch with the locking slide.

In another variation, the rotation of the rotatable collar may be limited (i.e., confined within a limited range). For example, the range of rotation may be limited to within 90 degrees, to within 60 degrees, to within 30 degrees, or to within 20 degrees or less. The partial rotation range may provide some capacity for the threaded interface on the rotatable collar to yield to unexpected rotational force or strain, but still position the collar within a range for easy engagement of the locking mechanism. Active biasing elements (e.g., elastic or spring loaded connections) may also be implemented to couple the rotatable collar to the housing, such that the receiving notch on the rotatable collar is aligned with the locking mechanism when no external rotation force is applied on the rotatable collar.

In another variation, the fluid line connector 2 comprises a safety connector locking luer fitting 48 designed to interface with a standard male locking luer fitting 50, as shown in FIG. 3A. A rotating thread section 52 freely rotates on the female connector housing barrel section 54. A cross-sectional view is provided in FIG. 3B. The rotation may be limited within a range for locking slide 56 engagement. In another variation, the rotating thread section 52 may rotate freely. A plurality of notches may be implemented on the rotating thread section for receiving the locking slide. The rotating thread section may be configured on a rotatable collar.

In this particular variation, the locking slide 56 is spring biased in the distal direction. The receiving notch 58 is configured with a slanted profile 60 matching the proximal end 62 of the locking slide 56. In the retracted position, the tip of the locking slide 56 engages part of the receiving notch 58. In this position the rotating thread section's clockwise rotation is restrained, allowing the male luer connector 50 to be threaded thereon. Once the male luer connector 50 is threaded onto the rotating thread section 52, the rotating thread is displaced proximally, and the rotation force overcomes the resistance from the proximal tip of the locking slide to allow the rotating thread section and the male luer connector to continue to rotate as a unit in the clockwise position. The design may prevent the user from over or under tightening of the threaded interface. The user may be instructed to rotate the male luer connector until the rotation tension overcomes the locking slides resistance such the further rotation result in free rotation in the clockwise direction. Thus, the user knows that proper tightening has not been achieved if clockwise rotation of the male luer connection continues to result in advancement of the male luer onto the female connector. Once the male luer connector 50 fully engages the rotating threads 52, further torque being applied by the user will result in free rotation of the male luer connector 50 in the clockwise direction, and prevent further tightening of the thread.

Once the male luer connector 50 engages the rotating thread section 52, counterclockwise rotation of the male luer connector results in the rotation of the rotating thread section 52. Since the notch 58 has a slanted profile 60 matching the proximal end of the locking slide 56, the locking slide 56 provides only minimal resistance to the counterclockwise rotation of the rotating thread section 52, thus preventing the male luer connector 50 from unthreading. Once the male luer connector 50 fully engages the rotating thread section, the male luer connector 50 can be freely rotated in the clockwise or counterclockwise direction while continuing to maintain the fluid channel established between the male 50 and the female 48 luer connector, as shown in FIG. 4A. Removal of the male luer connector 50 is accomplished by advancing the locking slide 56 proximally to engage the receiving notch 58 on the rotating thread section 52 to prevent any rotation. The male luer connector 50 can then be removed by rotating it counterclockwise in relation to the female luer connector 48, as shown in FIG. 4B.

In another variation, the under cut 64 of the ledge 66, which secures the rotatable collar 52 to the housing 68, may include a surface profile configured to minimize friction between the rotatable collar 52 and the ledge 66. For example, the under cut 64 of the ledge 66 may include a surface profile comprising a plurality of valleys 70, 72, such that contacting surface between the rotatable collar 52 and the ledge 66 is decreased in comparison to a flat surface interface. This decrease in surface contact can reduce the friction between the rotatable collar and the ledge, thereby allowing the rotatable collar to revolve more readily.

In yet another variation, the locking slide 56 shown in FIG. 4A may be spring biased such that the distal end of the locking slide 56 is partially positioned within the receiving notch 58 on the rotating thread section, and displacement of the locking slide 56 in the distal direction requires a positive force to overcome the spring bias. In this particular design, when the rotating thread section 52 is being rotated in the clockwise direction, the right edge of the locking slide 56 engages the notch 58, preventing the rotating thread section 52 to rotate and allowing the male luer connector 50 to be threaded onto the rotating thread section 52. When the rotating thread section 52 is rotated in the counterclockwise direction, the rotation force is directed onto the slanted profile 62 at the distal end of the locking slide 56, forcing the locking slide 56 out of the receiving notch 58, and allowing the rotating thread section 52 to rotate, thereby preventing the unthreading of the male luer connector 50. In order to disconnect the male luer connector 50, a positive pressure in the proximal direction is directed to keep the locking slide 56 in the receiving notch 58. As a result, the rotating thread section 52 is prevented from rotating and the male luer connector 50 can be unthreaded. In another variation, a plurality of receiving notches with slanted profiles may be implanted on the rotating thread section, such that when the rotating thread section is being rotated in the counterclockwise direction, the displaced sliding lock may engage an adjacent receiving notch after it has been displaced form the first receiving notch.

Figures 5A, 5B, 5C:
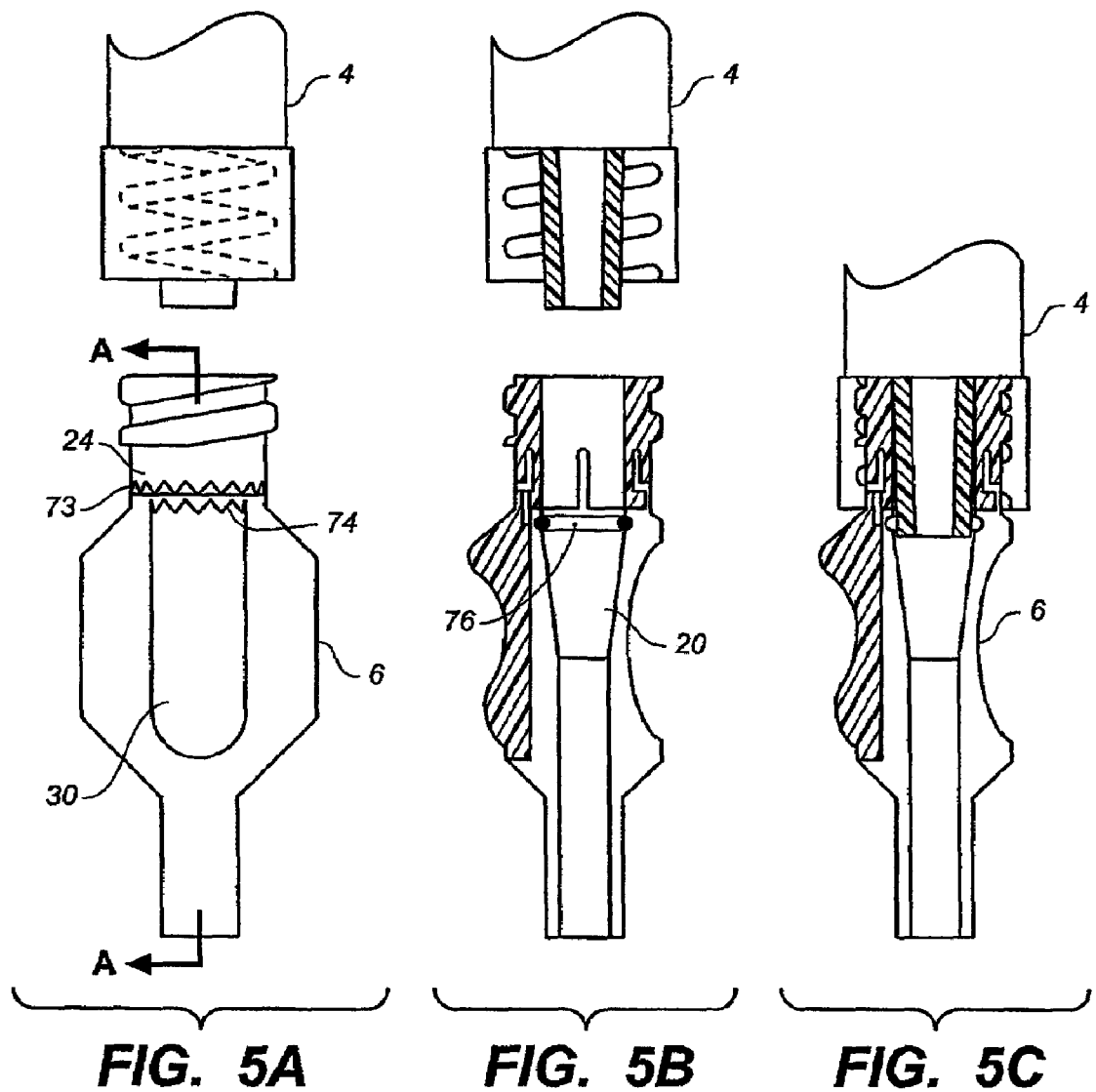
FIG. 5A illustrates another variation of a locking luer fitting. In this variation, the rotatable collar is provided with a jagged interface for engaging a locking slide with a corresponding jagged surface. This variation is configured such that the rotatable collar is able to rotate freely unless the locking slide is displaced proximally to engage the rotatable collar.
FIG. 5B is a cross-sectional view of the locking luer fitting of FIG. 5A with the male luer connector detached from the female luer connector. The cross-section is taken along "A-A" as shown in FIG. 5A.
FIG. 5C is the locking luer fitting of FIG. 5B shown with the male luer connector attached to the female luer connector.

In another variation, the proximal end 73 of the rotatable collar 24 is configured with a jagged surface (e.g., sawlike, multi-tooth configuration, etc.). A locking slide 30 with a corresponding jagged surface 74 is provided such that the locking slide 30 can engage the rotatable collar 24 independent of the orientation of the rotatable collar 24, as shown in FIG. 5A. The rotatable collar 24 is allowed to freely rotate about the longitudinal axis 46 of the female luer connector 6. An optional elastomeric ring 76 may be provided in the lumen 20 of the female luer connector 6 to enhance the seal between the male luer 4 and the female luer 6 fitting, as shown in FIG. 5B. FIG. 5C illustrates the male luer connector 4 being fully threaded onto the female luer connector 6.

FIG. 6A is a side view of the female luer connector 6 illustrating the full rotation capability of the rotatable collar 24. This design allows the male luer connector 4, which is threaded onto the rotatable collar, to freely rotate about the longitudinal axis 80 of the female luer connector 6 in either the clockwise or counterclockwise direction. Thus, inadvertent disconnection of the luer connection may be prevented. In addition, since this design allows the male luer connector 4 to turn freely in relation to the female luer connector 6, kinking of the tubing lines attached to the male and the female luer connectors may also be minimized. FIG. 6B is a cross-sectional view showing the various parts that comprises the female luer connector 6 shown in FIG. 6A. FIG. 7 illustrates one variation where the locking slide 30 can be detached from the housing body 18 by sliding it out of its receiving channel 78 on the female luer connector 6. In another variation, the locking slide is either spring loaded or elastically coupled such that a positive pressure keeps the locking slide in the distal position within its receiving channel on the housing. To activate the locking slide, the user can apply a force to displace the locking slide in the proximal direction. FIG. 8A is a cross-sectional view of the rotatable collar 24 from FIG. 6A. FIG. 8B is the cross-sectional view taken at "B-B" of FIG. 8A, illustrating the jagged engagement interface 80 on the rotatable collar 24 being distributed circumferentially around the lumen 82 of the rotatable collar.

Figures 9A, 9B:
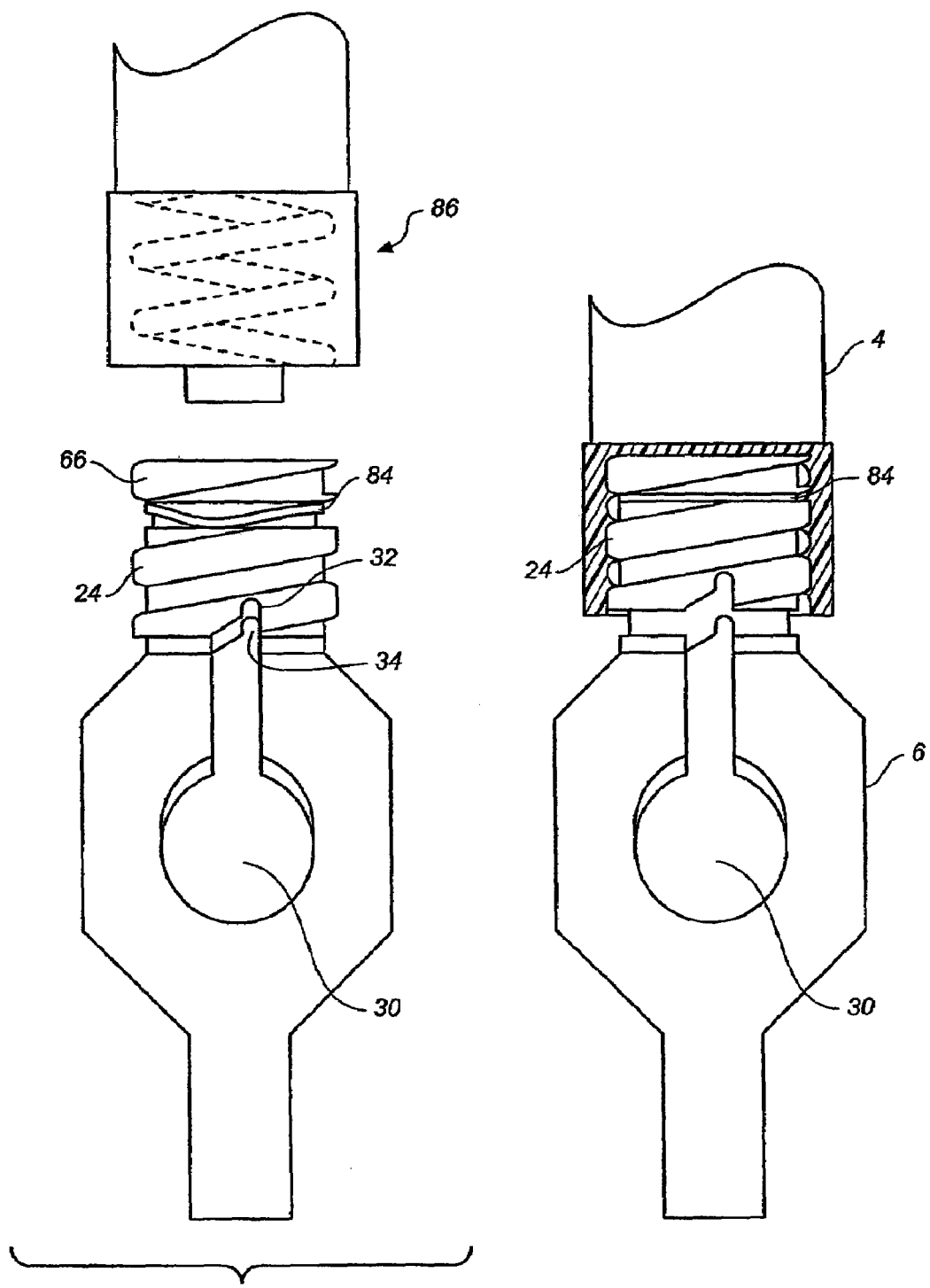
FIG. 9A illustrates another variation of a locking luer fitting where the rotatable collar is spring loaded and displaced proximally. The male connector is shown detached from the female connector.
FIG. 9B illustrates the locking luer fitting of FIG. 9A with the male connector connected to the female connector.

In another variation, the female luer connector further comprises a biasing mechanism (e.g., spring-loaded device, elastic materials, etc.) configured to actively displace the rotatable collar in the distal direction. FIG. 9A shows one particular design where the biasing mechanism 84 comprises a wave compression ring positioned between the ledge 66, which extends radially at the proximal end of the female housing, and the rotatable collar 24. The rotatable collar 24 is designed to interface with a standard locking luer fitting 86, as shown in FIG. 9B. When the male connector 4 is disconnected from the female connector 6, the rotatable collar 24 is fully displaced in the distal direction, as shown in FIG. 9A. As a result, a solid interaction may be established between the proximal end 34 of the locking slide 30 and the receiving notch 32 on the rotatable collar 24. This interaction prevents the rotation of the rotatable collar in the clockwise direction, thereby allowing the male luer connector to be threaded on the rotatable collar. As the male luer connector is being threaded onto the female luer connector, the rotatable collar is gradually displaced in the proximal direction due to the transfer of torque from the rotation of the male luer connector. As the rotatable collar is displaced in the proximal direction, the contacting surface between the locking slide 30 and the receiving notch 32 gradually decreases. Eventually, the rotatable collar 24 is displaced far enough in the proximal direction to allow the male luer lock connector 4 and the rotatable collar 24 to rotate in the clockwise direction. As a result, the connection between the male and the female luer connector cannot be further tightened. At this point, the male luer connector can be rotated freely in either the counterclockwise or the clockwise direction. To disconnect the male luer connector 4, the locking slide 30 is slid proximally toward the rotatable collar 24. The locking slide 30 locks the rotatable collar 24 into an aligned position allowing the male luer 4 thread to rotate in the counterclockwise direction and disconnect from the female connector 6.

Figure 10A:
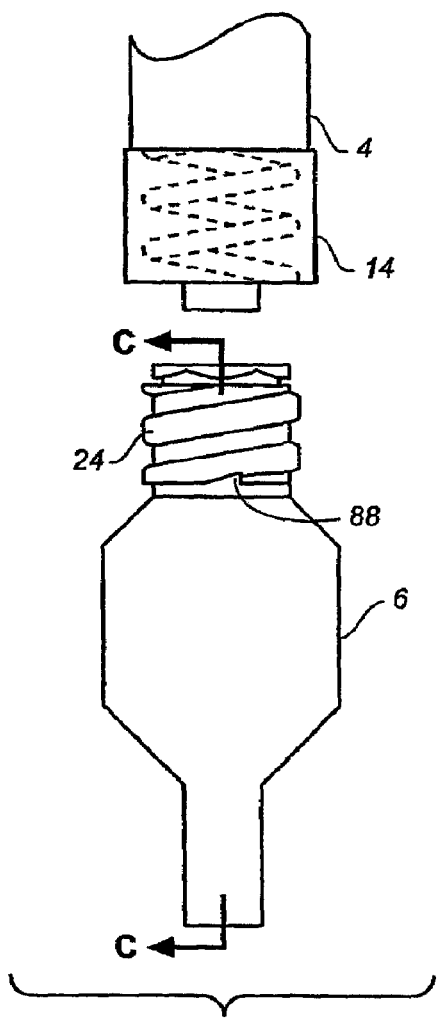
FIG. 10A illustrates another variation of a locking luer fitting utilizing a one way latch.
Figure 10B:
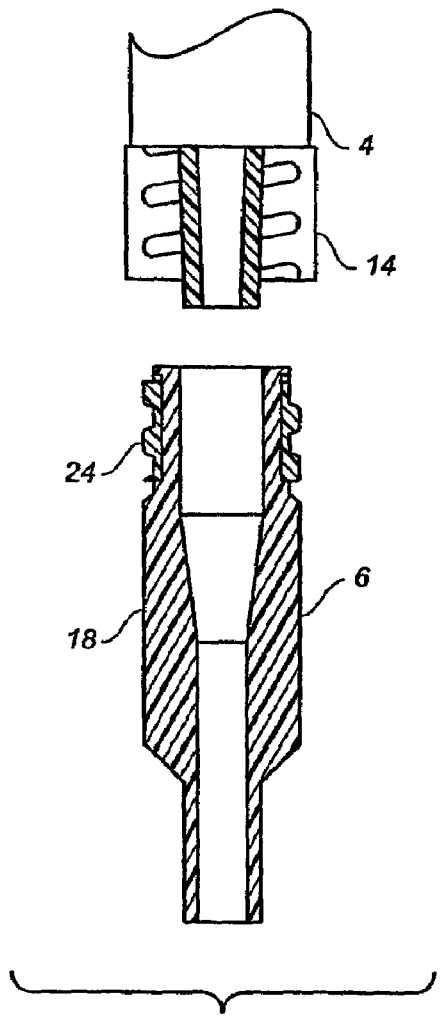
FIG. 10B is a cross-sectional view of the locking luer fitting of claim 10A. The cross-section is taken along "C-C" as shown in FIG. 10A.
Figure 11A:
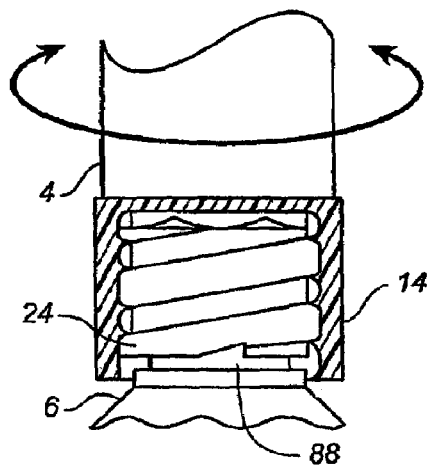
FIG. 11A illustrates the male connector and female connector of FIG. 10A connected to each other. The one way latch allows the male connector to rotate axially in relation to the female connector in both the clockwise and the counterclockwise direction.
Figure 11B:
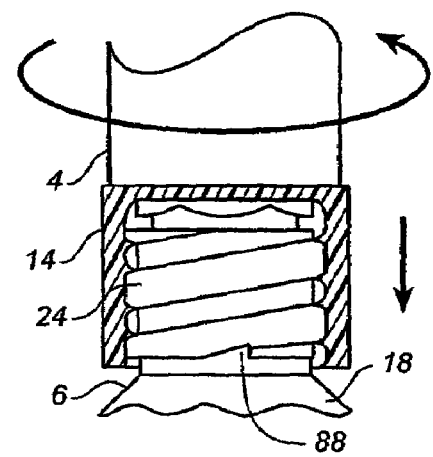
FIG. 11B illustrates the detachment of the male connector from the female connector. A positive pressure is applied to compress the male and female connector interface in order to engage the one way latch. The engagement of the one-way latch permits the user to unthread the male connector from the rotatable collar on the female connector.

In another variation, a one-way latch 88, which permits the counterclockwise rotation of the rotatable collar 24, is implemented, as shown in FIG. 10A. FIG. 10B is a cross-sectional view of the male 4 and female 6 connectors of FIG. 10A. The, clockwise rotation of the rotatable collar 24 is limited by the one-way latch 88, allowing a standard male luer connector to be threaded onto the rotatable collar on the female luer connector. As the locking collar 14 on the male connector 4 is threaded onto the rotatable collar 24 on the female connector 6, the rotatable collar 24 is gradually displaced in the proximal direction. Eventually, the rotatable collar 24 disengages from the one-way latch 88, such that the male luer connector 4 can rotate in both the counterclockwise and the clockwise position without unthreading the male and female luer connection. This helps to prevent the male luer connector 4 from unthreading when the male luer is subjected to unintended counterclockwise rotation. Removal of the male connector 4 is accomplished by pushing the male connector 4 against the female connector housing 18 while simultaneously rotating the male fitting 4 counterclockwise. The compression applied on the male connector 4 forces the rotatable collar 24 to engage the one-way latch 88 such that the male connector 4 can be unthreaded from the rotatable collar 24, as illustrated in FIG. 11B.

As one of ordinary skill in the art having the benefit of this disclosure would appreciate, other one-way latch mechanisms commonly know in the industry may also be implemented in the above design. For example, mechanisms commonly utilized in the child proof bottle cap designs may also be utilized as a one-way latch in variations of the locking luer fitting.

In another variation, the female luer connector has a threaded portion that comprises two segments. The lower thread segment can be rotated to misalign its threads with the corresponding threads on the upper segment. The misalignment of the threads on the female connector can cause a camming action that locks the threads on the attached male connector to the lower segment of the misaligned threads on the female connector.

In one example, the female connector 90 comprises a rotating locking collar 92 disposed around the housing 94 of the female connector 90. An upper thread segment 96 is positioned at the proximal end 98 of the housing 94, while a corresponding lower thread segment 100 is positioned on the rotating locking collar 92, as shown in FIG. 12A. FIG. 12B shows the side view of the corresponding male 102 and female 90 connectors from FIG. 12B. When the rotating locking collar 92 is aligned with the housing 94 of the female connector 90, the upper thread segment 96 is misaligned with the lower thread segment 100. To engage the male connector, the rotating locking collar 92 is first rotated as shown in FIG. 13, causing the threads on the upper thread segment 96 to align with the threads in the low thread segment 100. In one variation, the rotational movement of the rotating locking collar 92 is limited to about 20 degrees. Once the upper 96 and lower 100 thread segments on the female luer are aligned, the male connector 102 can be threaded on to the two segments 96, 100 of aligned threads located on the female connector 90. After the male connector 102 has been threaded onto the two aligned thread segments 96, 100, the user then rotates the rotating locking collar 92 so that the rotating locking collar becomes aligned with the housing 94, thereby causing the lower thread segment 100 to misalign with the upper thread segment 96. The misalignment of the lower and upper thread segment causes the threads on the female connector to cam lock against the fitting threads on the male connector. This camming action prevents the male connector from being unthreaded from the female luer connector. To release the male connector 102, the user first rotates the rotating locking collar 92 to align the threads on the upper 96 and lower 100 thread segments on the female connector 90. Once the threads on the upper 96 and the lower 100 thread segments are aligned, the male connector 102 is unthread with only minimal resistance.

In another aspect of the present invention, the fluid line connector comprises a locking cam that prevents inadvertent disconnection of the luer connectors. The male portion of the connector comprises a hollow elongated cylinder with a tapered mating surface at a distal portion of the cylinder. A locking collar is positioned around the distal portion of the hollow elongated cylinder, and the locking collar includes a threaded inner surface. The female portion comprises a housing, including a lumen configured for receiving the distal portion of the hollow elongated cylinder. The lumen includes an inner surface which matches the tapered mating surface of the cylinder. The distal portion of the housing includes a cylindrical outer surface. On the cylindrical outer surface is a threaded profile for engaging the threaded inner surface on the locking collar. A cam is slidably disposed on the cylindrical outer surface of the housing. When the male portion is threaded onto the female portion, the cam can be displaced to apply a camming force on the male portion of the connector and prevent the male portion from inadvertent disengagement from the female portion of the fluid line connector. To disconnect the male portion, the cam is displaced in the opposite direction to release the camming force. Once the camming force is removed, the male portion can then be unthreaded from the female portion.

In one variation, the male portion of the connector comprises a traditional luer connector with a locking collar, and the female portion of the connector comprises a female luer fitting with a cam slidably positioned to engage the threads on the male luer connector. In one example, the cam comprises a partial ring with a tapered end that can be engaged to prevent loosening (i.e., counterclockwise rotation) of the male luer connector once it is secured onto the female luer connector. Mechanisms for applying a counter rotational force to disengage the cam may also be integrated into the female luer connector.

Figure 14:
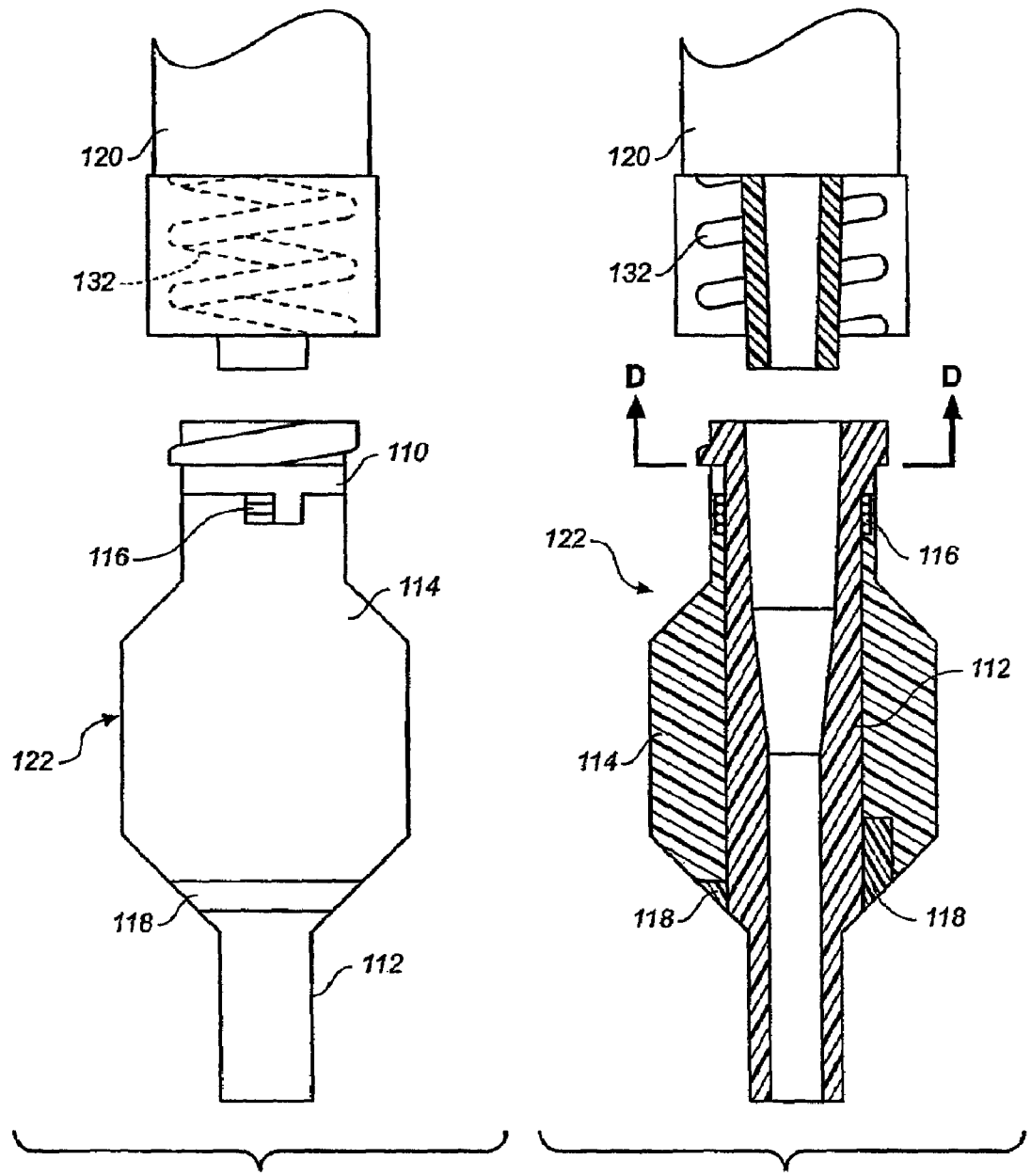
FIG. 14A illustrates another variation of a locking luer fitting implementing a sliding cam mechanism to prevent unintentional detachment of the male luer connector form the female luer connector.
FIG. 14B shows a cross-sectional view of the locking luer fitting of FIG. 14A.
Figure 15:
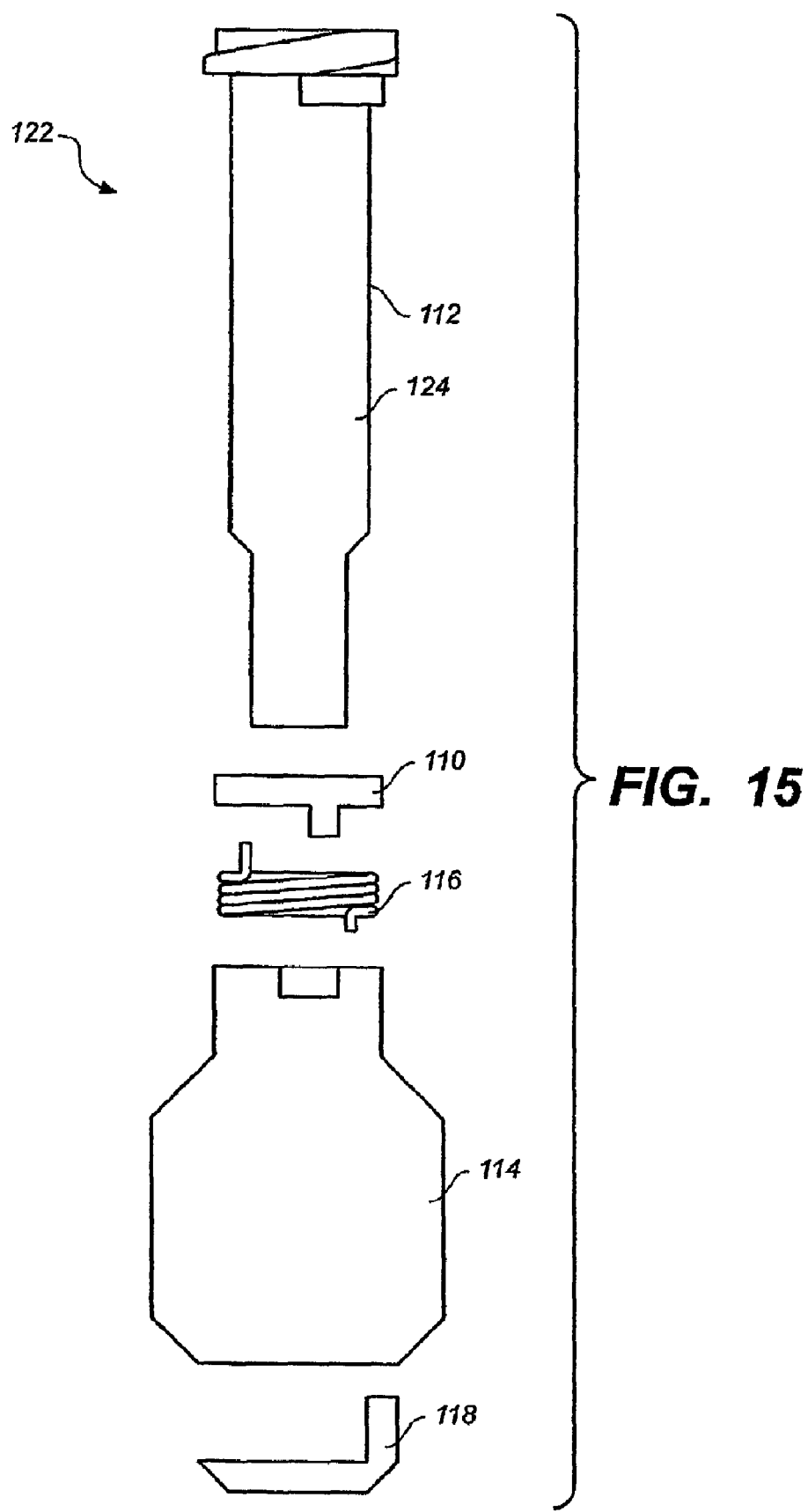
FIG. 15 illustrates the female connector of FIG. 14A in a disassembled condition.
Figure 18A:
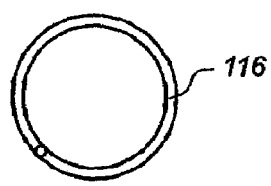
FIG. 18A shows a top view of the rotary spring from FIG. 15.
Figure 20A:
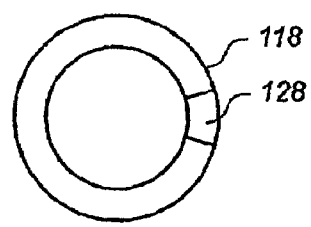
FIG. 20A is a top view of the retaining ring from FIG. 15.
Figure 18B:
FIG. 18B shows a side view of the rotary ring of FIG. 18A.
Figure 18C:
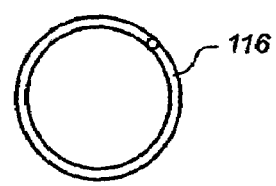
FIG. 18C shows a bottom view of the rotary ring of FIG. 18A.
Figure 20B:
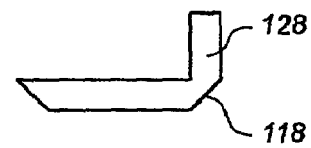
FIG. 20B is a side view of the retaining ring of FIG. 20A.
Figure 19A:
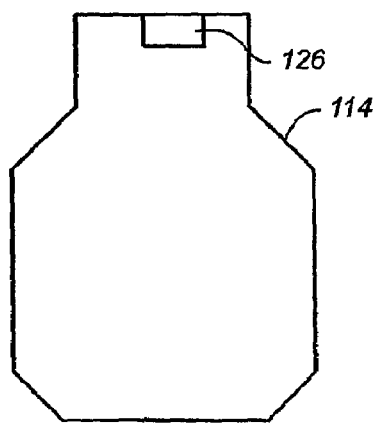
FIG. 19A is a side view of the rotating hub from FIG. 15.
Figure 19B:
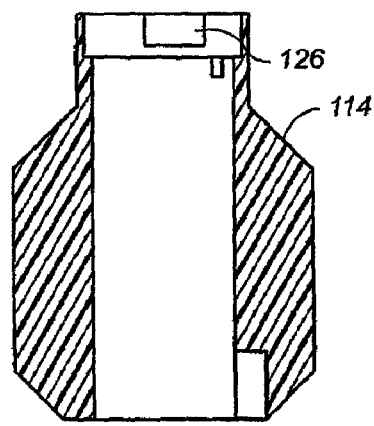
FIG. 19B is a cross-sectional view of the rotating hub of FIG. 19A.
Figure 19C:
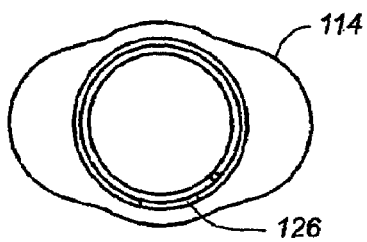
FIG. 19C is a top view of the rotating hub of FIG. 19A.
Figure 19D:
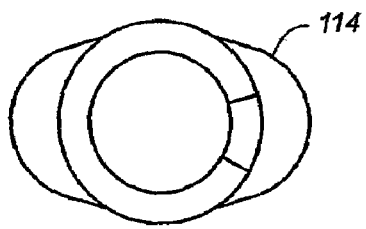
FIG. 19D is a bottom view of the rotating hub of FIG. 19A.

One particular design is illustrated in FIG. 14A. A partial ring 110 (serving as the cam) is rotatably disposed on an internal hub 112, and coupled to the rotating hub 114 for engaging the cam 110. The user can grasp onto the rotating hub 114 to apply a counter rotational force to disengage the locking cam ring 110 from the thread interface between the male 120 and the female 122 connector. FIG. 14B is a cross-sectional view of the corresponding male 120 and female 122 connector of FIG. 14A. FIG. 15 illustrates the female luer connector 122 with its parts disassembled. The female luer connector 122 comprises an internal hub 112 with a locking ring 110, a rotary spring 116, and a rotating hub 114, positioned over the outer circumferential surface 124 of the internal hub 112. A retaining ring 118 connected to the distal portion of the internal hub 112 secures the locking ring 110, the rotary spring 116, and the rotating hub 114 on the internal hub 112. The retaining ring 118 may be fixedly attached to the internal hub through solvent bonding, ultrasonic welding, or other methods that are well known to one of ordinary skill in art. FIGS. 16A-D illustrate various perspectives of the internal hub 112. FIGS. 17A-C illustrate various perspectives of the locking ring 110. FIGS. 18A-C illustrate various perspectives of the rotary spring 116. FIGS. 19A-D illustrate various perspective of the rotary hub 114. FIGS. 20A-B illustrate various perspectives of the retaining ring 118.

The rotary spring 116 applies a torsional force that biases the locking (cam) ring 110 in a counterclockwise (cam engaged) direction. Although a rotary spring 116 is implemented in this example, one of ordinary skill in the art having the benefit of this disclosure would appreciate that other biasing mechanisms may also be utilized in placed of the rotary spring 116. Rotational movement of the locking ring 110 is limited by the slot 126 on the rotating hub 114. The rotating hub's 114 movement is limited by the retaining ring tab 128. As an assembly, the locking ring 110 is biased to slide over the hub cam surface 130 of the internal hub 112. During the attachment of a male locking luer connection 120, the locking ring 110 does not expand over the hub cam surface 130. However, once the male connector 120 is attached, the camming action of the locking ring 110 prevents removal (unthreading) of the male luer connector 120. The device is configured such that the male luer connector 120 can be removed by grasping the rotating hub 114 while turning the male luer connector 120. This causes the locking ring 110 to be disengaged from the hub cam surface 130 and allowing free rotation of the threads 132.

Figure 21A:
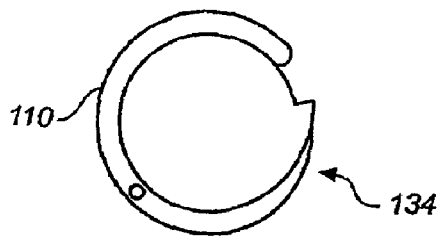
FIG. 21A illustrates the locking ring (i.e., slidable cam) in its default un-engaged position. This sectional view is taken at "D-D" as shown on FIG. 14B; the luer threads has been omitted in this illustration.
Figure 21B:
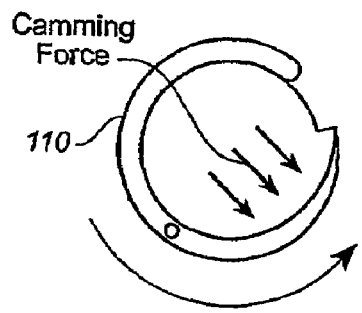
FIG. 21B illustrates the locking ring of FIG. 21A being rotated counterclockwise by 10 degrees and resulting in a camming force being exerted radially.

The mechanical interaction of the locking ring 110 in the above example is further illustrated in FIGS. 21A and 21B. FIG. 21A shows the locking ring 110 in the default un-engaged position (i.e., unlocked from the threads). Rotation of the male connector to unthread the male connector from the female connector engages the locking ring. As a result the locking ring 110 is rotated counterclockwise and forces the distal portion 134 of the outer surface of the locking ring to be displaced radially as the locking ring applies a camming force onto the thread surface 132 of the male connector. In one variation, the rotation of the locking rings is limited to about 10 degrees. The camming action of the locking ring locks the male connector onto the female connector. To release the male connector, the locking ring 110 is displaced in the clockwise direction which releases the camming force, allowing the male connector 120 to be unscrewed from the female connector 122.

Figure 22:
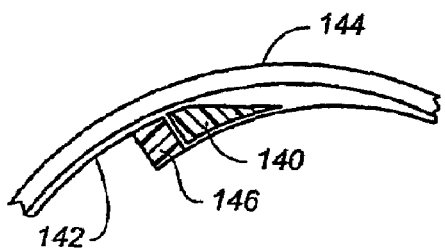
FIG. 22 illustrates another variation of a sliding cam comprising a wedge slidably disposed on the female connector to engage the threads from the male connector.

FIG. 22 illustrates another variation of a locking cam. In this design, a wedge 140 is slidably positioned on a surface on the female luer connector 142 that interfaces with the male luer connector 144. An optional biasing mechanism 146 may be implemented to predispose the wedge 140 such that the wedge engages the threads on the male connector 144 when the male connector is threaded onto the female connector 142. In one variation the wedge 140 is spring loaded. In another variation, a pliable polymeric block 146 is positioned between the wedge and the female connector housing, as shown in FIG. 22. As the male connector 144 threads onto the female connector 142 through a clockwise rotation, the wedge 140 is also displaced in the clockwise direction and engages the thread on the male luer connector 144. A counterclockwise rotational force on the male connector 144 faces a resistive force from the wedge 140 and loosening of the male connector 144 is averted. To release the male connector 144, the wedge 140 is first displaced in the counterclockwise direction to release the camming action. For example, the user may force the wedge 140 against the biasing mechanism 146 and disengage the wedge 140 from the threads (not shown) on the male connector 144. Once the cam 140 is disengaged, the user can rotate the male connector 144 in the counterclockwise direction to remove the male connector.

Figure 23:
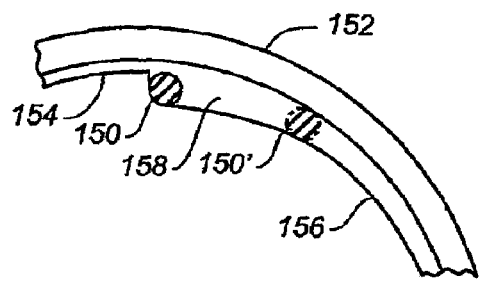
FIG. 23 illustrates another variation where a rolling cam is implemented to engage the threads on the male luer connector.

In another variation, a rolling cam 150 is implemented to prevent loosening of the male connector 152 once it is threaded onto the female luer connector 154. One example is illustrated in FIG. 23, where a rolling cam 150 is positioned on a circumferential surface 156 of the female luer connector 154. The rolling cam 150 is disposed within a pocket 158 including a curved profile. When the rolling cam 150 is in the cocked position 150', it engages the locking collar of the male luer connector 152. When the rolling cam 150 is displaced into the uncocked position 150, it sinks into the deeper portion of the pocket 158 and disengages from the male luer connector 152, allowing the removal of the male luer connector 152 through a counterclockwise rotation. The rolling cam 150 may be spring biased such that as the male connector is rotated onto the female connector, the rolling cam is activated. Levers or other coupling mechanisms may be implemented to allow the user to displace the rolling cam and keep it in the uncocked position, such that the male connector can be unthreaded from the female connector.

Coupling mechanisms well known to one of ordinary skill in the art may be implemented on the female luer connector, such that the user can apply the necessary force on the cam to displace and disengage the cam. In another variation, the female connector is designed so that a tool is needed to disengage the cam. For example, levers, which are coupled to the cam, may be integrated within the body of the female connector so that a tool is required activate the lever and release the cam. This design may prevent unintentional and/or unauthorized decoupling of the luer lock connection.

Figure 24:
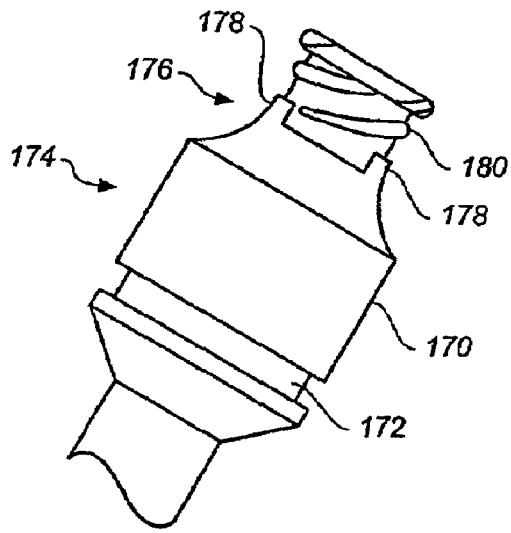
FIG. 24 illustrates another variation of female connector with a luer locking mechanism. In this variation, a slidable sleeve with a proximally positioned cam is provided to engage the male luer connector once the male luer connector is threaded onto the female luer connector.

In another variation, a cam slidably positioned on the female connector is configured for insertion between the locking collar of the male luer connector and the housing of the female luer connector after the locking collar of the male connector is threaded onto the female connector of the housing. The camming action locks the locking collar of the male connector in place and prevents the male connector from any rotation. In one example, a sleeve 170 is slidably disposed over the housing 172 of the female luer connector 174. The proximal portion 176 of the sleeve includes a camming surface 178. The sleeve 170 can be displaced in the proximal direction, as shown in FIG. 24. Once the male luer connector is threaded onto the female luer connector, the sleeve 176 is advanced in the proximal direction and the camming surface 178 on the proximal end of the sleeve 176 is inserted between the locking collar and the threaded portion 180 of the female housing 172. The camming force prevents the male luer connector from rotating in either direction and thus locking the male luer connector in place. To release the male luer connector, the sleeve 170 is displaced in the distal direction to release the camming action. Once the cam is removed, the male connector can then be unthreaded from the female connector.

Figure 25:
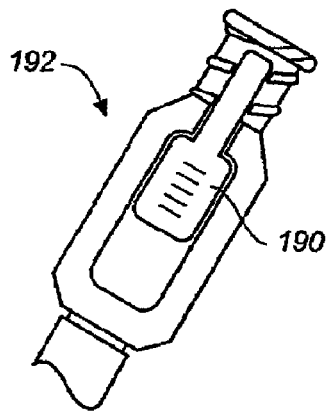
FIG. 25 illustrates yet another variation of a female connector with a luer locking mechanism. In this variation, a locking slide is provided to engage the threads on the male connector and lock the threads on the male connector in place.

In yet another design exemplified in FIG. 25, a locking slide 190 is utilized to engage the threads on the male connector to lock the male connector in place and prevent premature loosening of the male connector. The locking slide 190 may be biased in the proximal direction. To attach the male luer connector, the user first retracts the locking slide 190 in the distal direction and then screws on the male connector. Once the male connector is threaded onto the female connector 192, the user can advance the locking slide 190 in the proximal direction to engage the threads on the male connector and lock the threads in place. To remove the male connector, the user first retracts the locking slide 190. Once the camming action provided by the locking slide 190 is removed, the male luer connector can then be unthreaded from the female luer connector 192.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent that there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A fluid line connector to establish fluid communication with a conventional male luer fitting, comprising:
    a housing including an inner member, having a proximal opening adapted to receive a distal portion of the male luer fitting, and an outer member rotationally disposed about the inner member;
    a threaded profile circumscribing the proximal opening of the inner member adapted to interface with a threaded inner surface of a rotatable collar on the male luer fitting; and
    a cam member positioned about the inner member to engage the threaded inner surface of the rotatable collar, engagement of the cam member preventing disengagement of the male luer fitting from the housing.

2. The fluid line connector according to claim 1, further comprising a biasing member coupled to the cam member.

3. The fluid line connector according to claim 2, wherein the biasing member comprises a rotary spring that biases the cam member in a counterclockwise direction.

4. The fluid line connector according to claim 3, wherein rotation of the outer member in a clockwise direction displaces the cam member in a clockwise direction, permitting counterclockwise rotation of the male luer fitting to disengage from the housing.

5. The fluid line connector according to claim 1, wherein the cam member comprises a partial ring with a tapered distal end.

6. The fluid line connector according to claim 1, wherein the cam member comprises a tab configured for movement within a slot of the outer member, the slot limiting the range of rotation of the cam member.

7. The fluid line connector according to claim 1, further comprising a retaining ring attached to the inner member and configured to limit the degree of rotation of the outer member with respect to the inner member.

8. The fluid line connector according to claim 1, further comprising a protrusion disposed distal of the threaded profile on the inner member, a portion of the cam member positioned to slide over the protrusion.

9. The fluid line connector according to claim 1, wherein the cam member comprises a wedge disposed on the threaded profile of the inner member.

10. The fluid line connector according to claim 1, wherein the cam member comprises a rolling member disposed on the threaded profile of the inner member.

11. A fluid line connector, comprising:
    a housing including a hub member with a proximal opening adapted to receive a distal portion of a male luer connector and a threaded profile circumscribing the proximal opening adapted to interface with a threaded surface of a male luer connector collar; and
    a means for engaging the threaded surface of the collar to prevent de-coupling from the hub member by preventing rotation of the collar in a de-coupling direction, wherein the engaging means comprises a partial ring with a tapered distal end.

12. A fluid line connector, comprising:
    a housing including a hub member with a proximal opening adapted to receive a distal portion of a male luer connector and a threaded profile circumscribing the proximal opening adapted to interface with a threaded surface of a male luer connector collar; and
    a means for engaging the threaded surface of the collar to prevent de-coupling from the hub member by preventing rotation of the collar in a de-coupling direction, wherein the housing further comprises a protrusion disposed distal of the threaded profile on the hub member, a portion of the engaging means positioned to slide over the protrusion.

13. A fluid line connector, comprising:

a housing including a hub member with a proximal opening adapted to receive a distal portion of a male luer connector and a threaded profile circumscribing the proximal opening adapted to interface with a threaded surface of a male luer connector collar; and a means for engaging the threaded surface of the collar to prevent de-coupling from the hub member by preventing rotation of the collar in a de-coupling direction, wherein the engaging means comprises a wedge disposed on the threaded profile of the hub member.

14. A fluid line connector, comprising:

a housing including a hub member with a proximal opening adapted to receive a distal portion of a male luer connector and a threaded profile circumscribing the proximal opening adapted to interface with a threaded surface of a male luer connector collar; and a means for engaging the threaded surface of the collar to prevent de-coupling from the hub member by preventing rotation of the collar in a de-coupling direction, wherein the engaging means comprises a rolling member disposed on the threaded profile of the hub member.

15. A method for establishing fluid communication with a male luer fitting, comprising:

providing a fluid line connector including an inner member and an outer member rotationally disposed about the inner member, the inner member including a threaded profile circumscribing a proximal opening and a cam member positioned at least partially around the inner member on or adjacent the threaded profile; and threading a rotatable collar of the male luer fitting on the threaded profile by rotating the rotatable collar about the inner member in a first direction, the cam member preventing rotation of the rotatable collar in a second direction opposite the first direction by engaging a threaded inner surface of the rotatable collar.

* * * * *